United States Patent [19]

Cheng

[11] Patent Number: 5,798,254
[45] Date of Patent: Aug. 25, 1998

US005798254A

[54] GAS DRIVEN FERMENTATION METHOD USING TWO OXYGEN-CONTAINING GASES

[75] Inventor: Alan Tat Yan Cheng, Livingston, N.J.

[73] Assignee: Praxair Technology, Inc., Danbury, Conn.

[21] Appl. No.: 713,328

[22] Filed: Sep. 13, 1996

[51] Int. Cl.[6] ................................................. C12N 1/00
[52] U.S. Cl. ............................ 435/243; 435/813; 435/818
[58] Field of Search ................................. 435/243, 813, 435/818

[56] References Cited

U.S. PATENT DOCUMENTS

| | | | |
|---|---|---|---|
| 3,054,814 | 9/1962 | Jason et al. | 260/413 |
| 4,001,090 | 1/1977 | Kalina | 195/109 |
| 4,036,699 | 7/1977 | Quigg | 195/142 |
| 4,670,397 | 6/1987 | Wegner et al. | 435/289 |
| 4,782,024 | 11/1988 | Scott et al. | 435/247 |
| 5,356,600 | 10/1994 | Kiyonaga et al. | 422/234 |

*Primary Examiner*—David M. Naff
*Assistant Examiner*—Deborah K. Ware
*Attorney, Agent, or Firm*—Stanley Ktorides

[57] ABSTRACT

A gas driven fermentation method is disclosed wherein a gas, such as air, is passed heterogeneously upwardly through a fermentation broth to agitate and recirculate the broth. Further, the provision of oxygen for fermentation permits the carbon dioxide to be stripped off; and in addition a second gas, such as a fluid-containing oxygen is passed homogeneously upwardly through the broth to provide for supplemental air flow for the fermentation. The heterogeneously flow is carried out at a superficial velocity greater than 0.03 meter/second (m/sec); and the homogenous flow is carried out at a superficial velocity less than 0.05 m/sec.

4 Claims, 2 Drawing Sheets

6

GAS DRIVEN FERMENTATION METHOD USING TWO OXYGEN-CONTAINING GASES

TECHNICAL FIELD

This invention relates generally to fermentation systems and, more particularly, to fermentation systems which are driven by an injected gas such as air.

BACKGROUND ART

Fermentation is a chemical change induced by a living organism or enzyme, such as bacteria or the microorganisms occurring in unicellular plants, which involves the aerobic decomposition of hydrocarbons to produce a desired product along with carbon dioxide. Oxygen for the fermentation is generally supplied by the provision of air to the fermentation broth which is contained within a fermentation vessel. Fermentation systems are used for the production of a large number of products such as antibiotics, vaccines, synthetic biopolymers, synthetic amino acids, and edible proteins.

It is important that the contents within the fermentation vessel be in motion to ensure the efficient uptake of oxygen, proper distribution of nutrients and the continuous progression of the fermentation reaction to attain a good product yield. Generally such motion or stirring is provided by a mechanical agitation system. Mechanical agitation systems are complicated, costly, and prone to breakdown especially because, as the fermentation process proceeds, product builds up within the fermentation vessel and the thickness or viscosity of the fermentation broth increases.

In response to such problems with mechanically agitated fermenters, there has been developed gas driven fermenters wherein the requisite broth motion is provided by rising bubbles of gas introduced into the fermenter vessel to provide oxygen for the fermentation. Because this gas is usually air, such gas driven fermenters are generally termed air-lifted fermenters or air-lifted bioreactors. Such devices are also termed bubbling columns. The air causes the broth to rise in one region of the vessel and flow downward in another region of the vessel to form a recirculating flow of broth within the fermentation vessel.

Large volumes of air are needed to effectively agitate a commercial size air-lifted fermenter or bubbling column which can have a height of from 50 to 100 feet or more. As the air bubbles rise within the bubbling column they coalesce to form larger bubbles. The coalescence is rapid due to the large volume of air injected into the bubbling column. The gas rise velocity increases with bubble size as well as with height within the column. This increases the lifting action and the turbulence within the vessel. The violent agitation caused by rapidly rising large volume air bubbles is termed heterogeneous flow. This heterogeneous flow not only enhances the lifting action within the vessel but also serves to improve stripping the carbon dioxide, which is generated by the fermentation, out of the broth, which improves the fermentation rate.

While air-lifted fermenters have been very advantageous for use such as in the pharmaceutical and fine chemical industries, there can arise production problems caused by oxygen starvation of the fermentation reaction, especially with the use of more active biological agents that demand a lot of oxygen. There are practical limitations to how much more air one can add into an air-lifted bioreactor without blowing the contents entirely out of the reactor.

In order to address this production problem, the industry has employed the injection of an additional or supplemental oxygen-containing gas into the air-lifted fermenter to supply additional oxygen to the fermentation broth. In order to avoid having the supplemental gas bubbles coalesce with the air bubbles and thus negate the effect of the supplemental injection, the supplemental gas is provided into the air-lifted fermenter at a distance from the point where the air is provided. Often this supplemental gas is provided into the fermentation broth in the downflowing region of the vessel to assure that it is provided far from the rising air bubbles. However such a procedure reduces the circulation effect within the vessel because of the braking action of the supplemental gas bubbles which try to rise within the downflowing broth. While providing additional oxygen for the fermentation, this procedure reduces the lifting action and the carbon dioxide stripping action which are also needed to achieve high production.

Accordingly it is an object of this invention to provide an improved gas driven fermentation or bubbling column system wherein a supplemental gas may be used to provide additional oxygen for the fermentation while avoiding the detrimental effects experienced with conventional supplemental gas provision systems.

SUMMARY OF THE INVENTION

The above and other objects, which will become apparent to one skilled in the art upon a reading of this disclosure, are attained by the present invention, one aspect of which is:

A method for carrying out fermentation comprising:

(A) injecting a first oxygen-containing gas into the lower portion of a vessel containing a broth comprising a constituent capable of undergoing fermentation;

(B) passing said first oxygen-containing gas in a set of first bubbles upwardly through said vessel in a heterogeneous flow causing an upward flow of said broth;

(C) injecting a second oxygen-containing gas into the lower portion of said vessel and passing said second oxygen-containing gas in a set of second bubbles upwardly through said vessel in a homogeneous flow; and (D) utilizing oxygen from both the first oxygen-containing gas and the second oxygen-containing gas to carry out fermentation of said constituent.

Another aspect of the invention is:

Apparatus for carrying out fermentation comprising:

(A) a fermenter vessel;

(B) a first injector communicating with the interior of the fermenter vessel for injecting a first oxygen-containing gas into the fermenter vessel for passage through said fermenter vessel in a heterogeneous flow;

(C) a second injector communicating with the interior of the fermenter vessel for injecting a second oxygen-containing gas into the fermenter vessel for passage longitudinally through said fermenter vessel in a homogeneous flow; and (D) said second injector communicating with the interior of the fermenter vessel proximate where said first injector communicates with the interior of the fermenter vessel.

As used herein the term "heterogeneous flow" means flow having a nonuniform distribution of gas bubbles and characterized by the presence of large bubbles or agglomeration of bubbles. Heterogeneous flow does not occur at a superficial velocity less than 0.03 m/sec.

As used herein the term "homogeneous flow" means flow having a uniform gas bubble distribution and a narrow bubble size distribution wherein there is no observable gas/liquid downflow. Homogeneous flow does not occur at a superficial velocity greater than 0.05 m/sec.

As used herein the term "lower portion" means the portion of the fermenter vessel below the midpoint of the fermenter vessel.

As used herein the term "superficial velocity" means the quotient of the volumetric gas flow divided by the cross sectional area of the fermenter vessel or of the draft tube if a draft tube is employed within the fermenter vessel.

DETAILED DESCRIPTION

Figure 1:
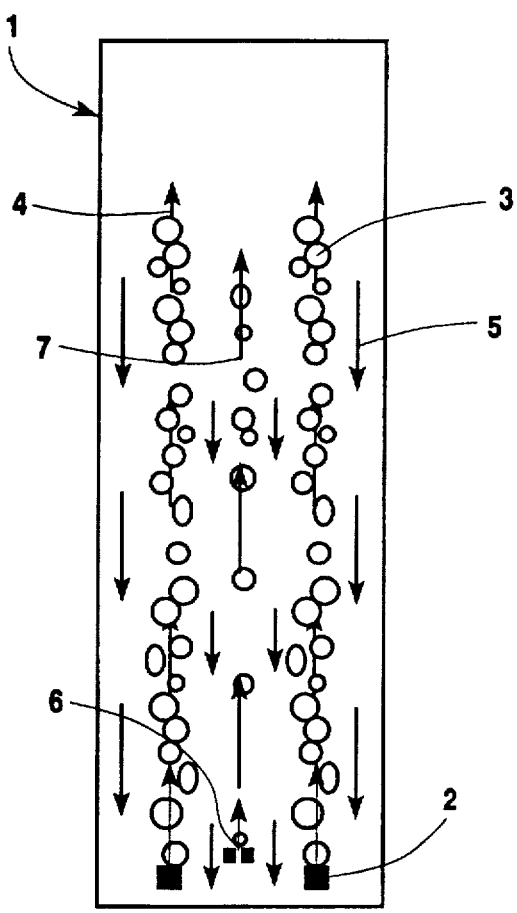
FIG. 1 is a cross-sectional stylized representation of the fermentation system of this invention.

The invention will be described in detail with reference to the Drawings. Referring now to FIG. 1, fermenter vessel 1 contains a broth containing at least one constituent capable of undergoing fermentation to produce a product. The broth generally comprises water, a nutrient or fermentable constituent such as corn syrup, molasses and glucose, and a biological agent such as bacteria, fungus and yeast. The broth may also contain additives such as antifoam agents, nitrates, pH adjustment chemicals and the like. Products which can be produced by the fermentation system of this invention include antibiotics such as penicillin, erythromycin and tetracycline, organic chemicals such as ethanol, sorbitol and citronellol, organic acids such as citric acid, tartaric acid and lactic acid, amino acids such as L-lysine and monosodium glutamate, polysaccharides such as baker's yeast and xanthan gum, vitamins such as ascorbic acid and riboflavin, and other products including enzymes, insecticides, alkaloids, hormones, pigments, steroids, vaccines, interferon and insulin.

A first oxygen-containing gas, which is generally and preferably air, is injected into the lower portion of vessel 1 through first injector 2. The gas rises through vessel 1 in a set of first bubbles 3. The first oxygen-containing gas, hereinafter also termed air for convenience, rises within vessel 1 in a heterogeneous flow, preferably at a superficial velocity greater than 0.05 meters per second (m/sec). Generally the flowrate of the air into fermenter vessel 1 will be within the range of from 10 to 400 standard cubic feet/liter-hr. where liter refers to the volume of the reactor or fermenter vessel. The heterogeneous flow of the air coupled with the large size of the rising air bubbles causes the broth to rise within vessel 1 as depicted by the upwardly pointing arrows 4. As the upwardly flowing broth approaches the top of vessel 1, it changes course and flows down vessel 1, as depicted by the downwardly pointing arrows 5, in a recirculating pattern. The turbulent, heterogeneous air flow and the recirculating broth combine to improve oxygen transfer from the air to the broth to drive the fermentation, and to remove carbon dioxide from the broth generated by the fermentation.

Second oxygen-containing gas, having an oxygen concentration exceeding that of the first oxygen-containing gas, is injected into the lower portion of vessel 1 through second injector 6. Preferably the second oxygen-containing gas has an oxygen-concentration of at least 30 mole percent, most preferably at least 80 mole percent. The second oxygen-containing gas may also be commercially pure oxygen having an oxygen concentration of 99.5 mole percent or more. For convenience the second oxygen-containing gas will hereinafter also be termed oxygen.

The oxygen is injected into vessel 1 proximate the point where the air is injected into vessel 1. That is, second injector 6 communicates with the interior of fermenter vessel 1 proximate where first injector 2 communicates with the interior of vessel 1. The oxygen is not required to perform the lifting and stripping action and thus has homogeneous flow.

The oxygen is injected into vessel 1 at a flowrate generally within the range of from 0.1 to 20 standard cubic feet/liter-hr. The oxygen rises through vessel 1 in a set of second bubbles 7 which are generally smaller in diameter, and larger in surface area to volume ratio, than are first bubbles 3. This improves the transfer of oxygen into the broth. The oxygen bubbles 7 rise through the broth within vessel 1 in a homogeneous flow, preferably at a superficial velocity less than 0.03 m/sec. and less than the superficial velocity of the rising air bubbles 3. It is an important aspect of this invention that the second oxygen-containing gas is not provided into the broth within the fermenter vessel at region where the broth is flowing downwardly. Rather, this second oxygen-containing gas is provided into the broth preferably where it is rising.

The upwardly flowing oxygen bubbles 7 flow close to air bubbles 3 but, owing to the homogeneous nature of their flow, do not coalesce substantially with the air bubbles. Thus a large fraction of the oxygen within the small bubbles 7 passes out of the oxygen bubbles and into the broth to drive the fermentation. It is expected that from about 25 to 75 percent of the oxygen needed for the fermentation is derived from the oxygen bubbles with the rest coming from the air bubbles. When the bubbles reach the top of the reactor, they generally pass out of the reactor along with stripped carbon dioxide and other gases.

As the fermentation reaction progresses and product builds up within the fermenter vessel, the thickness or viscosity of the broth increases, up to 800 centipoise (cps) or more. The invention has particular utility when the viscosity of the broth exceeds 10 cps and especially when it is at least 100 cps because the difference in gas flow characteristics, i.e. homogeneous versus heterogeneous flow, is particularly effective within such a high viscosity broth to keep the two sets of gas bubbles separate, without coalescing, as they rise through the fermenter vessel. Generally the fermentation process will be a batch process and when the process is completed, the product will be withdrawn from the fermenter vessel, separated and generally further processed.

Figure 2:
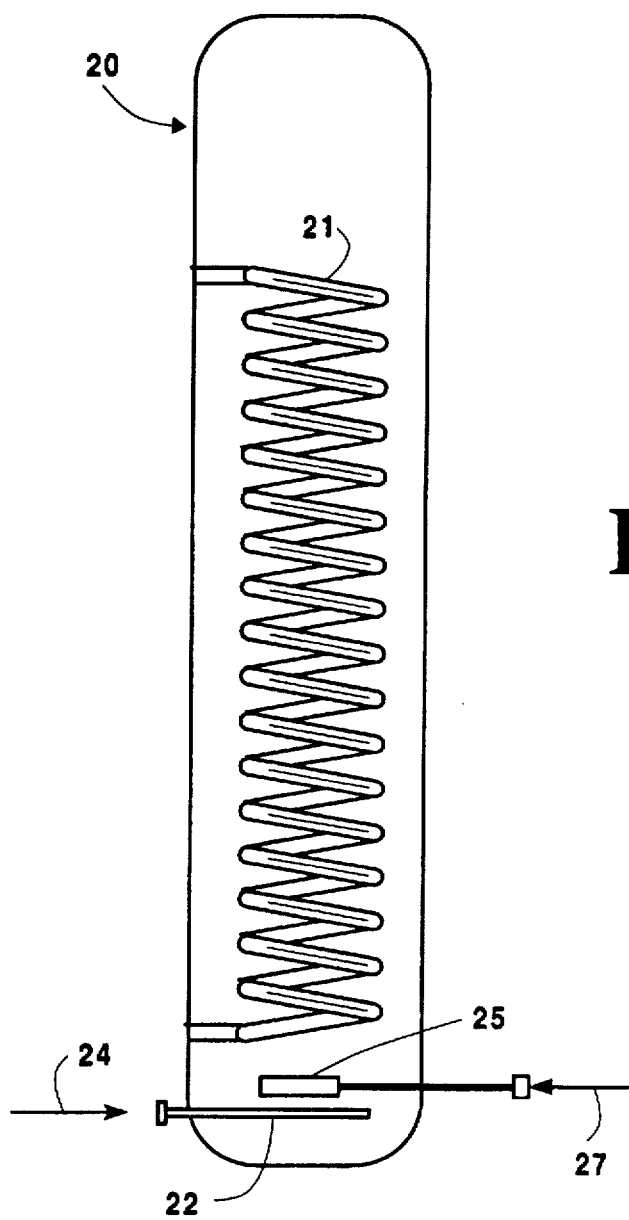
FIG. 2 is a simplified cross-sectional elevation view of one embodiment of the fermentation apparatus of this invention.
Figure 3:
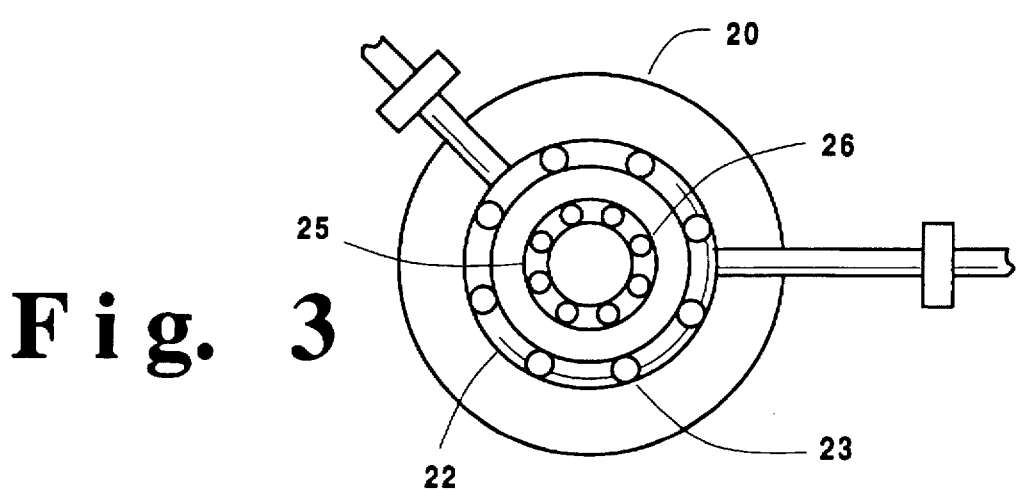
FIG. 3 is an overhead view of one embodiment of the injectors useful in the practice of this invention.

FIGS. 2 and 3 illustrate one preferred embodiment of the fermentation apparatus of this invention. The numerals in the Figures are the same for the common elements. Referring now to FIGS. 2 and 3, fermenter vessel 20 is a cylindrical column having a height or longitudinal length generally within the range of from 10 to 100 feet, and a diameter generally within the range of from 12 to 200 inches. If desired, as illustrated in FIG. 2, fermenter vessel 20 may contain a cooling coil 21 around its internal periphery to maintain the temperature of the fermenting broth within desired limits. Fermenter vessel 20 is generally made of metal, such as stainless steel.

In the lower portion of fermenter column 20 below cooling coil 21 is air sparger 22 which comprises a ring having six equispaced injectors or nozzles 23 and which communicates with a source of air 24. Oxygen sparger 25 is located proximate sparger 22, slightly above and within the circumference of sparger 22. Sparger 25 comprises a ring having twelve equispaced 10 injectors or nozzles 26, which are smaller than nozzles 23, and communicates with a source of oxygen-containing gas 27 having an oxygen concentration of 30 mole percent or more. Air and oxygen are injected into column 20 through spargers 22 and 25 respectively, and bubble up through the fermentation broth contained within column 20 in the manner previously described.

Figure 4:
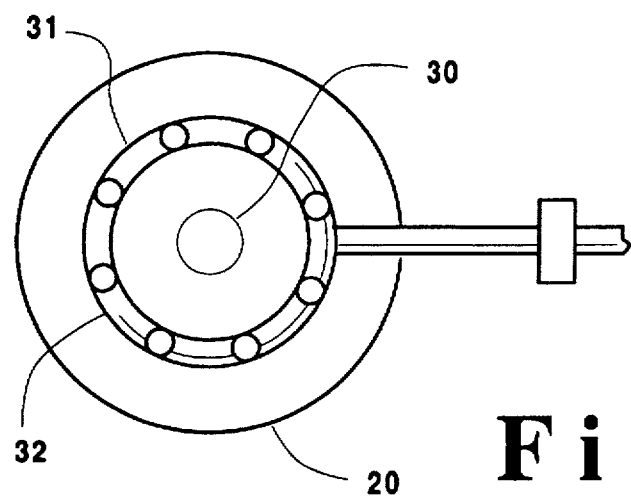
FIG. 4 is an overhead view of another embodiment of the injectors useful in the practice of this invention.

FIG. 4 illustrates another embodiment of the injectors useful with the invention wherein the air is injected through a single central nozzle 30 and the oxygen is injected through sparger 31 which is a ring which circles nozzle 30. Sparger 31 is preferably at the same level as nozzle 30 although it may be slightly above or below the injection point of nozzle 30. Sparger 31 comprises a ring having a plurality of equispaced injectors or nozzles 32 and communicates with a source of oxygen-containing gas. Nozzles 32 are each smaller than nozzle 30 which communicates with a source of air.

As mentioned, it is an important aspect of this invention that the second injector communicates with the interior of the fermenter vessel proximate where the first injector communicates with the interior of the fermenter vessel. When the injector system comprises concentric sparger rings such as is illustrated in FIG. 3, this proximate communication can be described by r being within the range of from 0.25A to 0.5A where r is the radius of the oxygen sparger ring and A is the radius of the air sparger ring. When the injector system comprises a central air nozzle and an oxygen sparger ring such as is illustrated in FIG. 4, this proximate communication can be described by r being within the range of from 0.5R to 0.75R where r is the radius of the oxygen sparger ring and R is the radius of the fermenter vessel.

Now, by the use of this invention, one can effectively provide supplemental oxygen into a gas lifted fermentation broth to maintain a high fermentation rate and increase product yield without impediment to the gas lifting action. Although the invention has been described in detail with reference to certain preferred embodiments, it will be understood by those skilled in the art that there are other embodiments of the invention within the spirit and the scope of the claims. For example, the fermenter vessel may contain other internal structures such as baffles or a draft tube, i.e. a cylinder open at both ends longitudinally oriented within, and spaced from both the top and the bottom of, the fermenter vessel. When a draft tube is used, it is preferred that the gas injectors be arranged so that both the air bubbles and the oxygen bubbles flow upwards within the interior of the draft tube.

I claim:

1. A method for carrying out fermentation comprising:

(A) injecting a first oxygen-containing gas into the lower portion of a vessel containing a broth comprising a constituent capable of undergoing fermentation;

(B) passing said first oxygen-containing gas in a set of first bubbles upwardly through said vessel in a heterogeneous flow having a superficial velocity greater than 0.03 m/sec causing an upward flow of said broth;

(C) injecting a second oxygen-containing gas into the lower portion of said vessel and passing said second oxygen-containing gas in a set of second bubbles upwardly through said vessel in a homogeneous flow having a superficial velocity less than 0.05 m/sec; and (D) utilizing oxygen from both the first oxygen-containing gas and the second oxygen-containing gas to carry out fermentation of said constituent.

2. The method of claim 1 wherein the first oxygen-containing gas is air.

3. The method of claim 1 wherein the second oxygen-containing gas is a fluid having an oxygen concentration of at least 30 mole percent.

4. The method of claim 1 wherein the size of the bubbles in the second set of bubbles is smaller than the size of the bubbles in the first set of bubbles.

* * * * *